United States Patent [19]

Himmele et al.

[11] 4,168,270

[45] Sep. 18, 1979

[54] TRIPINYLTRIOXANES

[75] Inventors: Walter Himmele, Walldorf; Hardo Siegel, Ludwigshafen, both of Fed. Rep. of Germany

[73] Assignee: BASF Aktiengesellschaft, Fed. Rep. of Germany

[21] Appl. No.: 627,611

[22] Filed: Oct. 31, 1975

[30] Foreign Application Priority Data

Nov. 7, 1974 [DE] Fed. Rep. of Germany ....... 2452804

[51] Int. Cl.$^2$ .......................................... C07D 323/04
[52] U.S. Cl. .................................................. 260/340
[58] Field of Search ........................................ 260/340

*Primary Examiner*—Norma S. Milestone
*Attorney, Agent, or Firm*—Keil & Witherspoon

[57] ABSTRACT

Tripinyltrioxanes of the general formula (I):

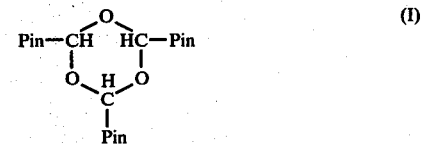

in which the radicals Pin are either dextrorotatory (+) or laevorotatory (−) pinyl radicals; a process for the production of (I) by treatment of an enantiomeric mixture of (+)-3-formylpinane and (−)-3-formylpinane (II) with an acid in an organic solvent and fractional precipitation of the trimeric compound (I); and redissociation of (I) into the pure enantiomers (II) with a catalytic amount of an acid.

1 Claim, No Drawings

TRIPINYLTRIOXANES

The present invention relates to tripinyltrioxanes of the general formula (I):

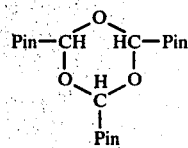
(I)

in which the radical Pin is either a dextrorotatory (+) or laevorotatory (−) pinyl radical, to processes for their production and to their redissociation into the corresponding 3-formylpinanes.

U.S. Pat. No. 4,081,477 (application Ser. No. 544,306) relates inter alia to 3-formylpinanes and a method of producing them by hydroformylation of α-pinenes.

α-pinene is known to exist in the two optically isomeric forms:

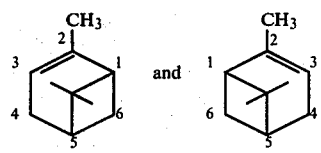

the endo-2,2-propylene group here and hereinafter being regarded as being above the plane of the paper and the carbon atoms in positions 1 and 5 being regarded as being in the plane of the paper.

When these compounds are subjected to hydroformylation with a rhodium catalyst, the corresponding 3-formyl pinanes (II) are obtained, the structure of the molecules remaining intact but the direction of rotation changing.

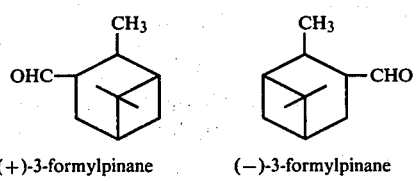
(II)

(+)-3-formylpinane     (−)-3-formylpinane

The commercial α-pinene used as starting material for the production of the formylpinanes always consists of a mixture of the two enantiomers and depending on the origin one form generally predominates. Consequently hydroformylation gives an analogous mixture of isomers.

It is the object of the present invention to prepare the two optical isomers of 3-formylpinane in an economical manner in a pure form because 3-formylpinanes are used for syntheses of organic compounds in which optical isomerism plays an important part (for example the derivatives of 3-formylpinanes are very suitable for racemate resolution) and because optically pure formylpinanes are valuable perfumes.

We have found that this object is achieved by treating an enantiomeric mixture of (+)-3-formylpinane and (−)-3-formylpinane in an organic solvent with an acid, fractionally precipitating the resultant tripinyltrioxanes of the general formula (I):

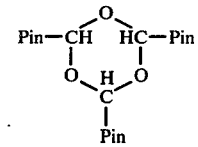
(I)

in which Pin is either a dextrorotatory (+) or laevorotatory (−) pinyl radical or allowing them to crystallize out, and redissociating these fractions, with or without another fine fractionation, by means of a catalytic amount of acid so that the enantiomers are obtained in pure form.

The process according to the invention is based on the observation that trimeric formylpinanes, i.e. the compounds (I), are built up almost exclusively of optically identical isomers, that the two isomers of (I) thus obtainable exhibit only a slight tendency to form mixed crystals and that the original pinane skeleton remains intact under the conditions of the redissociation.

Suitable organic solvents in which the trimerization of the 3-formylpinanes may be carried out are generally those with which the starting compounds cannot react under the process conditions, in which they have good solubility over a temperature range from −10° to +40° C. and in which the trimers exhibit an appreciable solubility gradient over this range. Weakly polar oxygen-containing solvents such as alkylcarboxylic acid esters or dialkyldicarboxylic acid esters, dialkyl ketones and dialkyl ethers in each case of from three to eight carbon atoms have proved to be particularly suitable. Examples of such solvents are: ethyl acetate, butyl acetate, methyl propionate, isopropyl acetate, isobutyl formate, dimethyl malonate, dimethyl succinate, diethyl ketone, methyl isopropyl ketone, methyl n-propyl ketone, di-n-butyl ether and diisopropyl ether.

The amount of solvent required varies according to the nature of the solvent. In the case of ethyl acetate the amount of solvent used in conveniently from about 0.1 to 1 kilogram per kilogram of 3-formylpinane; in the case of the other solvents the ratios are similar or may be ascertained without difficulty by a few preliminary tests.

Medium strength and strong acids are particularly suitable for the trimerization provided they are soluble in the solvent in the necessary concentrations—from about 0.1 to 5% by weight of solvent depending on the strength of the acid. For example hydrogen chloride and strong organic acids such as oxalic acid and the chloroacetic acids have proved to be suitable. Good results are also achieved however with strongly acid ion exchangers because the acid reagent can be separated in this case after the trimerization is over.

The trimerization is preferably carried out at a temperature of from −10° to +40° C. and it should be remembered that an equilibrium reaction is involved in which the equilibrium is displaced in favor of the trimers as the temperature falls. Various convenient procedures, depending essentially on economic factors, result from this fact and from the fact that the trimer is more sparingly soluble than the monomer. At low temperatures the amount of solvent is gauged so that the trimer is precipitated during the trimerization. The fraction first deposited approximates very closely to the rotation of the optically pure isomer (50° in benzene) and as the degree of deposition increases the purity of the whole of the trimers deposited up to this point naturally deteriorates. It has however proved to be convenient economically to tolerate a lower purity down to about a rotation of 42° (this can readily be monitored by taking samples) because purity can easily be increased by subsequent recrystallization. At the said rotation the amount of trimer precipitated is about equal to the fraction of the isomer present in the predominant amount, i.e. if the original mixture of 100 parts of formylpinene contains for example 80 parts of one isomer, precipitation can be carried to about 80 parts of trimer. The separation effect in this procedure is sufficient for a further purification stage but the yield is high and the reaction is rapid.

When using higher temperatures the whole of the trimer formed is at first kept in solution. Since the trimerization is appreciably exothermic, the end of it can be recognized by the fact that no further heat is developed. The solution is then conveniently allowed to cool to ambient temperature, if necessary after solid constituents such as ion exchanger have been separated. Seed crystals of the optically pure tripinylpinane which is present in the predominant amount are then added, and the whole is stirred for some time at ambient temperature and then cooled by about 20° to 30° C. Since the enantiomer which is not stimulated to crystallize has a strong tendency to remain in solution it is easy to control the crystallization so that about 60% of the desired isomer is obtained in a purity of from 96 to 98%. In this case however the yield is less than in the abovementioned more rapid procedure.

Which of the two methods is preferred in principle or whether a combination of these methods is chosen will depend mainly on what purity of the desired isomer is finally aimed at.

In both cases the 3-formylpinane consisting of its two optical antipodes need not be particularly pure. According to our observations so far, up to about 15% of byproducts stemming from the hydroformylation does not disturb the process according to the invention. The solvent containing acid may be placed in a vessel and the 3-formylpinane gradually added while stirring or the acid may be added rapidly to a solution of the 3-formylpinane while stirring. The mother liquor may be processed in an analogous manner into the other isomer.

It is advisable to wash the crystals obtained in the trimerization and also in the recrystallization in order to remove adherent mother liquor and to decrease the acid content. For example solutions of potassium hydroxide in methanol are suitable for a neutralizing preliminary washing and methanol is suitable for afterwashing.

The pure tripinyltrioxanes (I) melt at 156° to 158° C. and exhibit an optical rotation of $[\alpha_D] = +$ or $-50.0°$ in benzene.

The seed crystals may be prepared in the simplest way by appropriate modification of the said procedure.

For the preparation of the optically pure 3-formylpinanes the compounds (I) are dissociated by known methods of polyacetal cleavage by means of a catalytic amount of an acid. Suitable acids are the same acids as for the trimerization and also weaker acids. Since it is convenient to remove the monomeric aldehyde from the dissociation mixture immediately after its formation it is advisable to heat the compound (I) in pure form with a sparingly volatile acid such as preferably oxalic acid (it is true that this sublimes but it is immediately precipitated again so that it gives no particular trouble) at subatmospheric pressure at the boiling temperature of the 3-formylpinane so that it is distilled off. Strong sparingly volatile acids such as phosphoric or sulfuric acid are less suitable because they cause a certain amount of rearrangement in the pinane skeleton.

The optically pure 3-formylpinanes are valuable compounds for asymmetric organic syntheses. Among other things their derivatives such as the 3-aminomethylpinanes are particularly suitable for the resolution of racemates because of their ready accessibility.

The trimeric 3-formylpinanes are stable and less reactive than the monomeric aldehydes so that they can be stored better in this form than in the monomeric form.

The following Examples illustrate the invention.

EXAMPLE 1

1000 g of a mixture of about 80% of (+)-3-formylpinane, 15% of (−)-3-formylpinane and 5% of byproducts (obtained by hydroformylation of α-pinene) is added in the course of two hours to 500 g of ethyl acetate containing 1.3% of hydrogen chloride at ambient temperature while stirring. The temperature rises to 34° C. The reaction mixture is stirred for another four hours at ambient temperature. Then a few seed crystals of trimeric (+)-3-formylpinane are added and the whole is again stirred for fourteen hours. It is then cooled to −3° C., 520 g of the trimeric (+)-3-formylpinane crystallizing out.

Recrystallization from 1500 g of ethyl acetate gives the chemically pure compound in a yield of 42% based on the amount of monomeric aldehyde used. The melting point is 156° to 158° C.; $[\alpha]_D = 50.0°$ (benzene).

For redissociation 425 g of the trimer has 5 g of oxalic acid added to it and is heated to 121° C. in the course of two hours. Distillation at this temperature and 35 mm Hg gives pure (+)-3-formylpinane in a yield of 96%.

EXAMPLE 2

As described in Example 1 there is first prepared from 1000 g of a mixture of about 80% of (+)-3-formylpinane, 13% of (−)-3-formylpinane and 7% of contaminants the trimer of (−)-3-formylpinane (yield 35%) and from this the monomer (yield 95%).

EXAMPLE 3

Tri-(+)-pinyltrioxane is prepared in a 60% yield analogously to Example 1 but with 15 g of oxalic acid as the trimerizing agent.

EXAMPLE 4

As described in Example 1 (but with 2000 g of a 3-formylpinane mixture containing 85% of the (+)-isomer and with 500 g of ethyl acetate containing 1.3% of hydrogen chloride) the trimeric aldehyde is prepared in a 52% yield. After having been washed three times, each time with 200 g of ethyl acetate, it has a purity of more than 98% as determined by measuring the angle of rotation.

EXAMPLE 5

A solution of 600 g of (+)-3-formylpinane (about 85%) and 200 ml of butyl acetate is saturated at 0° C. with hydrogen chloride (equivalent to an absorption of HCl of about 15 g) and stirred for 2.5 hours. Tripinyltrioxane is thus precipitated. Precipitation is stopped as soon as the rotation of the crystals has reached a value of $\alpha_D = 43.8°$ (benzene). This is equivalent to a degree of precipitation of about 82% based on the whole amount of formylpinane used.

The crystal mash is washed with a solution of potassium hydroxide in methanol and with methanol and recrystallized once from butyl acetate. Redissociation of the compound analogously to Example 1 gives the pure (+)-3-formylpinane in a yield of 70% based on the content of this isomer in the starting material.

We claim:

1. A tripinyltrioxane of the general formula (I):

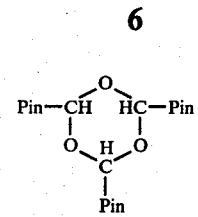

in which the radicals Pin are either dextrorotatory (+) or laevorotatory (−) pinyl radicals.

* * * * *